(12) United States Patent
Skov

(10) Patent No.: US 8,109,359 B2
(45) Date of Patent: Feb. 7, 2012

(54) EAR PROTECTOR

(75) Inventor: Roman Skov, Stuttgart (DE)

(73) Assignee: Moldex-Metric, Inc., Culver City, CA (US)

( * ) Notice: Subject to any disclaimer, the term of this patent is extended or adjusted under 35 U.S.C. 154(b) by 0 days.

(21) Appl. No.: 12/442,873

(22) PCT Filed: Oct. 8, 2008

(86) PCT No.: PCT/EP2008/008499
§ 371 (c)(1),
(2), (4) Date: Apr. 29, 2009

(87) PCT Pub. No.: WO2010/040367
PCT Pub. Date: Apr. 15, 2010

(65) Prior Publication Data
US 2011/0174320 A1    Jul. 21, 2011

(51) Int. Cl.
*H04R 25/02* (2006.01)
(52) U.S. Cl. ......................................................... 181/130
(58) Field of Classification Search .................... 181/130
See application file for complete search history.

(56) References Cited

U.S. PATENT DOCUMENTS

| | | | | |
|---|---|---|---|---|
| 3,661,225 A | * | 5/1972 | Anderson | 181/175 |
| 3,845,505 A | * | 11/1974 | Davison et al. | 2/209 |
| 3,895,627 A | * | 7/1975 | Leight | 128/865 |
| 4,461,290 A | * | 7/1984 | Gardner et al. | 128/866 |
| 4,671,265 A | * | 6/1987 | Andersson | 128/866 |
| 4,819,624 A | * | 4/1989 | Leight et al. | 128/866 |

(Continued)

FOREIGN PATENT DOCUMENTS
EP    0587925    3/1994
(Continued)

OTHER PUBLICATIONS

PCT/EP2008/008499 International Search Report dated Dec. 12, 2008, 4 pages.

(Continued)

*Primary Examiner* — Forrest M Phillips
(74) *Attorney, Agent, or Firm* — Charles H. Schwartz

(57) ABSTRACT

The invention describes an ear protector (1) comprising a resilient band (2), the free ends of which each have arranged thereon an earplug (4). The band (2) includes a first area (2a) whose center line (2a') merges under an angle α with an additional area (2b). When in use, the band is pivotable in the user's ears about an axis of rotation (3') extending through the earplugs (4). In order to implement such an ear protector in a structurally simple manner such that noise disturbance caused when the band (2) rubs on a piece of clothing can be reduced or eliminated, it is suggested to implement a chin area (2a) and a cheek area (2b) between which the angle α is provided, said angle α ranging from 35° to 90°, preferably from 45° to 70° and even more preferably from 50° to 60°. The length (L) of the cheek area (2b) is dimensioned such that an extension of the center line (2a') of the chin area (2a) and a line (5), which is parallel to said center line (2a') and which extends through the point of penetration (D) of the axis of rotation (3') through the band (2), are spaced apart at a distance (A) which ranges from 30 to 80 mm, preferably from 40 to 60 mm and even more preferably from 45 to 55 mm.

13 Claims, 3 Drawing Sheets

U.S. PATENT DOCUMENTS

Figure 1:
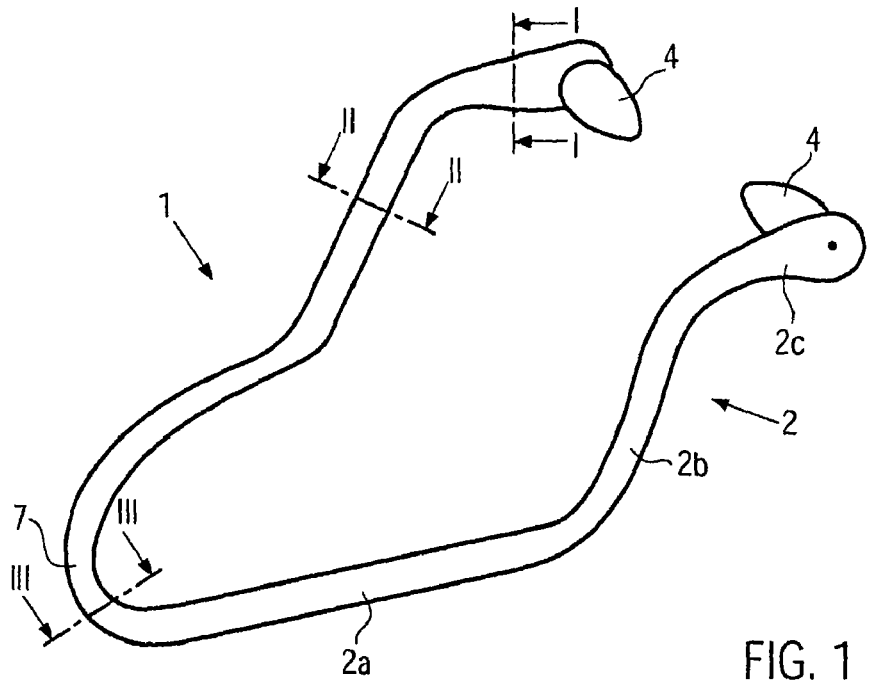

| | | | |
|---|---|---|---|
| 5,298,691 A | * 3/1994 | Leight | 181/135 |
| 5,824,966 A | * 10/1998 | Leight | 181/130 |
| 6,138,790 A | * 10/2000 | Leight | 181/130 |

FOREIGN PATENT DOCUMENTS

| | | |
|---|---|---|
| EP | 0911004 | 4/1999 |
| EP | 1457182 | 3/2004 |
| EP | 1927330 | 6/2008 |
| WO | 98/06363 | 2/1998 |
| WO | 98/20820 | 5/1998 |
| WO | 98/49984 | 11/1998 |

OTHER PUBLICATIONS

EP 07 01 7422 European Search Report dated Jan. 24, 2008, 2 pages.

* cited by examiner

EAR PROTECTOR

The present invention relates to an ear protector of the type specified in the preamble of claim 1.

A large number of such ear protectors is known, e.g. from EP 911 004, which has been taken into account in the preamble, or from EP 836 841 or EP 870 487. The known ear protectors have essentially the same design principle. They comprise a resilient band with two free ends having each secured thereto an earplug. When the ear protector is put on, the band is slightly pulled apart so that the earplugs are firmly pressed into the user's outer ear canal when the stress on the band is subsequently relieved. The bands are implemented such that, when in use, they are located below the chin, i.e. between the chin and the throat. The bands comprise a front area which, in the case of all the ear protectors according to the above-described publications, extends along the chin and the cheeks up to a point close to the user's ear where it merges under an angle with another area defining the connection to the user's ear. This additional area is bent such that a free space for the user's earlobe is provided so that the latter will not rub on the band when the user's head moves relative to the band. All the ear protectors according to the above-mentioned publications are implemented such that the transition between these areas is located comparatively close to the user's ear, since the free space is required only there. For avoiding contact with the earlobe, angles between 20 and 30° are shown in all the above-described publications. In EP 911 004 an angle of 30° is mentioned. However, this comparatively large angle does not primarily serve to provide a free space for the earlobe but serves to protect the earplugs against soiling, when this ear protector is laid onto a plane surface. Due to this angle of 30°, the earplugs are reliably raised from the surface. This, however, will only work when the transition between the first and second areas is located comparatively close to the earplug, since, otherwise, the weight of the earplugs would tilt the band and the aimed-at purpose of keeping the earplugs away from the surface would not be achieved.

All the known ear protectors entail the problem that the bands are sound-conducting to a certain extent, and this will be unpleasant when the band rubs on the clothes, e.g. on the collar. In order to solve this problem, it has already been suggested in EP 836 841 that the band should be produced from two materials of different hardness so as to achieve an interruption of sound conduction. This embodiment is, however, comparatively complicated and therefore expensive to produce, and this is definitely disadvantageous in the case of mass products having a limited service life.

It is therefore the object of the present invention to provide an ear protector which reduces, in a structurally simple manner, noise disturbance caused when the band strikes, in particular, against the collar and pieces of clothing.

This object is achieved by the features disclosed in claim 1.

The structural design according to the present invention reduces noise disturbance by an enhanced freedom of neck movement, i.e. an enlarged distance between the band and the neck when the ear protector is in use, the band being divided into two clearly distinguishable areas; the cheek area guarantees the necessary vertical distance between the ear and the chin area so that the chin area can be angled such that it will lie just below the chin, whereby the risk of contact with the collar of a piece of clothing is substantially reduced. This structural design has the effect that the contour of the band in the chin and cheek areas is basically adapted to the contour of the lower jaw bone of an adult, the chin area following the corpus mandibulae and the cheek area following the ramus mandibulae. In addition, this structural design has the effect that the centre of gravity of the whole ear protector is slightly displaced towards the ear and the neck, respectively, when the ear protector is in use, so that the essentially horizontally projecting chin area can be held more effectively in the horizontal position by the friction of the earplugs in the user's ears and is, even in the case of vibrations, prevented from automatically swivelling downwards towards the user's collar.

Advantageous further developments of the present invention are disclosed in the subclaims.

Figures 1A, 1B, 1C:
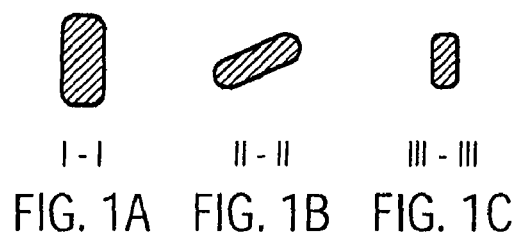
Figure 2:
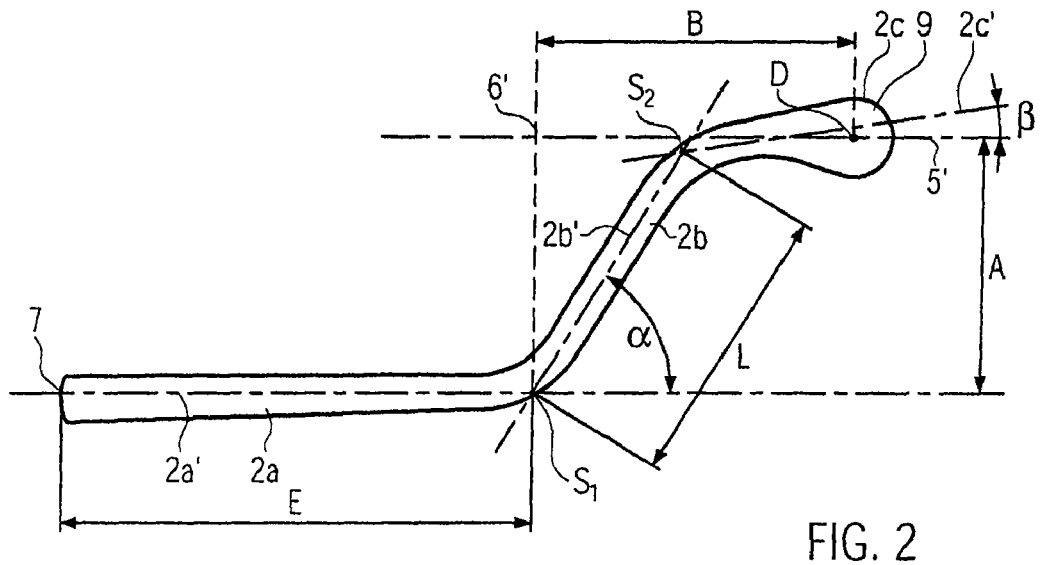
Figure 3:
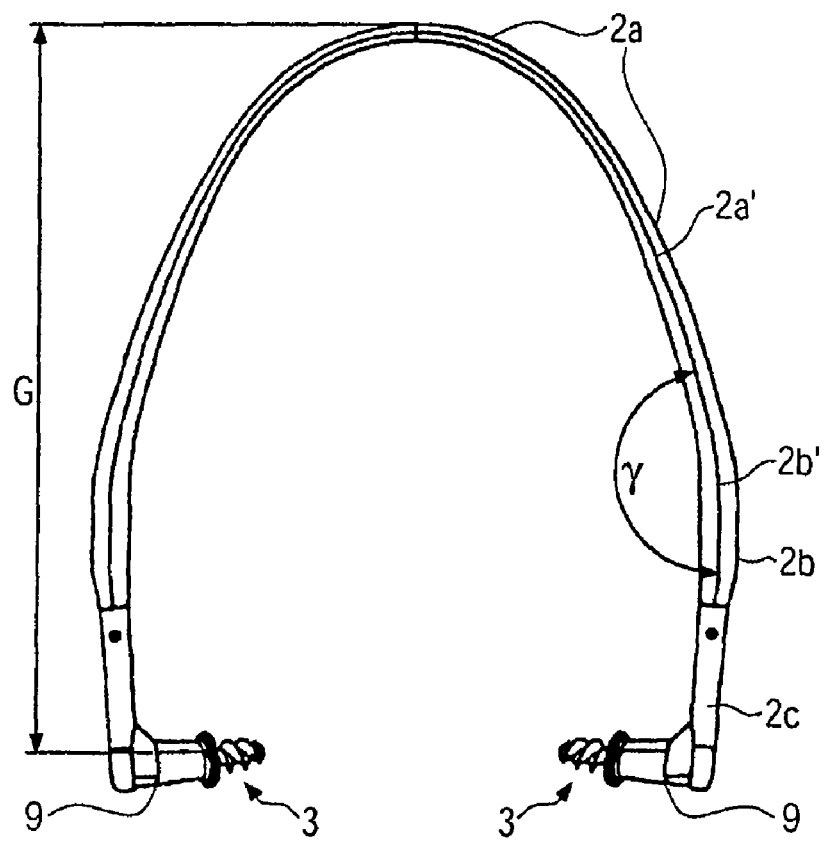
Figure 4:
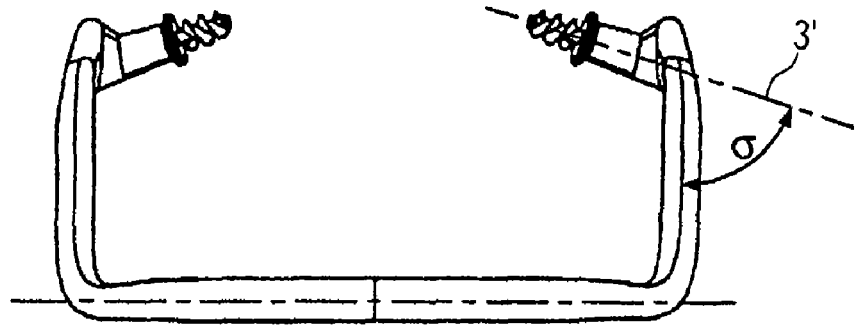
Figure 5:
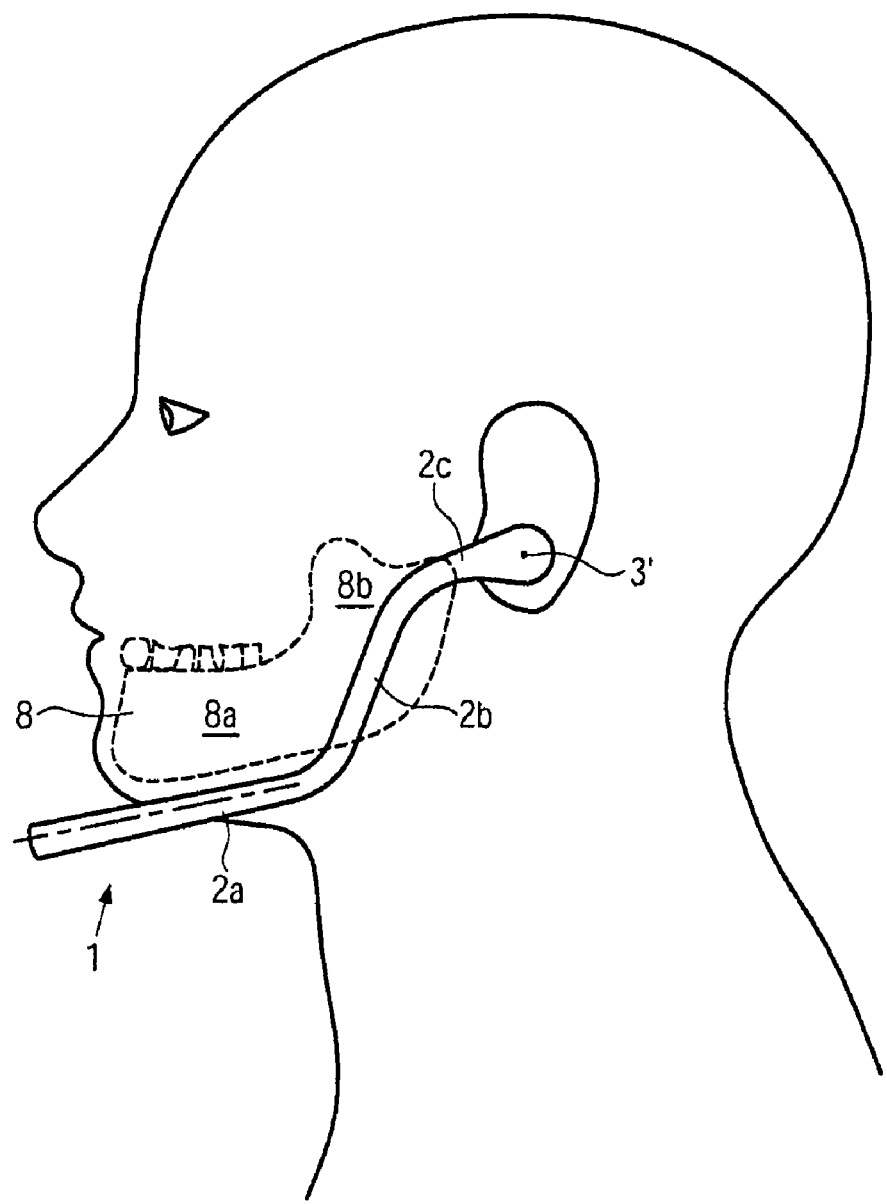

In the following, an embodiment of the present invention will be explained in detail making reference to the drawings, in which:

FIG. 1 shows a perspective representation of an ear protector according to the present invention, FIG. 1A, 1B, 1C show sectional views I-I, II-II and III-III according to FIG. 1, FIG. 2 shows a side view of the ear protector according to FIG. 1, FIG. 3 shows a top view of the ear protector according to FIG. 1, FIG. 4 shows a front view of the ear protector according to FIG. 1, and FIG. 5 shows the ear protector according to FIG. 1 in a position of use.

The figures show in a schematic representation an ear protector 1 according to the present invention, which comprises a band 2 produced from one of the conventional materials, in particular plastic material, which have already been used for such bands up to now. The band 2 is implemented as an elongate element having substantially the shape of a horseshoe when seen from above (FIG. 3), and includes at each of its two free ends a support 3 having secured thereto an earplug 4 that consists preferably of noise-absorbing materials, in particular of a plastic foam. The fastening of the earplugs 4 is preferably releasable so that the earplugs can be replaced when they are worn or dirty. The earplugs 4 are adapted to the anatomic conditions in the outer ear canal of adult users.

In the embodiment shown, the support 3 includes a threaded part, preferably with a large pitch and acute-angled, comparatively sharp-edged turns, said threaded part being introduced by a screwing movement into an opening provided in the earplug 4. The opening of the earplug need not necessarily be provided with a mating thread for this purpose, but the thread turn of the support will incise the material of the earplug 4, provided that the difference between the diameter of the opening in the earplug 4 and that of the thread of the support is sufficiently large. In addition, the thread of the support 3 is preferably conical in shape or it is provided with a pointed tip after the fashion of wood screws. Fastening of the earplugs 4 by means of a thread can, however, also be used in the case of conventionally shaped bands.

The support 3 is secured to the band 2 at an anatomically conditioned spatial angle, other than 90°, such that it is directed upwards and slightly forwards (direction during use) and defines an axis of rotation 3' about which the earplug 4 can rotate in the user's ear when the band 2 is pivoted during use.

In the no-load condition, the band 1 is shaped such that the earplugs 4 are held in oppositely spaced relationship with one another, the distance between the earplugs 4 being smaller than the width of the head of a user wearing the ear protector. It follows that, for using the ear protector 1, the band must be pulled apart to such an extent that the earplugs 4 can be inserted into the user's ears. When the user lets go of the band, the latter will resiliently return to a position where the earplugs 4 are pressed into the user's ears.

FIG. 1 to 4 show the band 2 in a relaxed, no-load condition, the dimensional and angular conditions described hereinbelow referring also to the no-load, i.e. undeformed state.

The band 2 of the ear protector 1 according to the present invention comprises at least a chin area 2a and a cheek area 2b as well as preferably a connection area 2c which is located close to the user's ears. These three areas 2a to 2c can clearly be differentiated from one another due to their position relative to one another.

The chin area 2a has a centre line 2a' and extends in one plane. When seen from above, the chin area 2a is substantially parabola-shaped, i.e. it is curved such that it narrows at the front, adapted to the line of curvature of a human lower jaw. The chin area 2a is followed by a cheek area 2b on either side. The cheek area 2b extends obliquely upwards from the chin area 2a, the centre lines 2b' of the cheek area 2b extending at an angle α relative to the centre line 2a' of the respective adjoining part of the chin area 2a. The angle α ranges from 35° to 90°, preferably from 45° to 70° and even more preferably from 50° to 60°. In a specially preferred embodiment the angle α is an angle between 53° and 58°.

The cheek area 2b is preferably straight and arranged and dimensioned such that an extension of a centre line 2a' of the chin area 2a and a line 5', which is parallel to said centre line 2a' and which extends through a point of penetration D of the axis of rotation 3' through the band 2, are spaced apart at a distance A, which ranges from 30 to 80 mm, preferably from 40 to 60 mm and even more preferably from 45 to 55 mm. In a preferred embodiment this distance amounts to 45 mm.

Furthermore, the point of penetration D of the axis of rotation 3' through the band 2 is spaced apart from a line 6', which extends at right angles to the centre line 2a' of the chin area 2a through the point of intersection S1 of said centre line 2a' with the centre line 2b' of the cheek area 2b, at a distance B which ranges from 55 to 90 mm, preferably from 60 to 80 mm and even more preferably from 65 to 75 mm.

The cheek area 2b has along its centre line 2b' between the point of intersection S1 of the centre line 2b' with the centre line 2a' of the chin area 2a and a point of intersection S2 with the centre line 2c' of the connection area 2c a length L which ranges from 40 to 65 mm, preferably from 45 mm to 55 mm and even more preferably from 47 mm to 53 mm. In a preferred embodiment this length L amounts to 50 mm.

The connection area 2c extends from the cheek area 2b substantially parallel to the chin area 2a, the deviations from parallelism being less than 5°. This means that the angle β between the centre line 2c' of the connection area 2c and the centre line 2a' of the chin area 2a, or rather the line 5' which extends parallel to said centre line 2a' is an angle between 0 and 5°.

The individual areas 2a, 2b, 2c merge with one another via respective curved portions. The length E of the chin area 2a between a connection line extending between the points of intersection S1 and the middle 7 of the chin area 2a, which is located farthest away from the earplugs 5, is a length between 30 mm and 100 mm, preferably 60±30 mm. The overall length G of the ear protector 1 between the earplugs 4 (at the point of penetration D) and the middle 7 is, when seen from above, preferably a length of approx. 135 to 165 mm, and even more preferably 135 mm to 155 mm, and most preferably 145.

The band 2 normally has an elongate, rectangular cross-section, the orientation of the longer side of the cross-section, and possibly the length and width, varying, however, along the band due to the different areas. In the connection area 2c, for example, the cross-section is arranged such that its long side is vertically oriented, as shown in FIG. 1A. In the cheek area 2b the cross-section is substantially horizontal to oblique, i.e. it is gently inclined inwards, as shown in FIG. 1C. The chin area 2a has, in turn, a substantially vertically extending cross-section (FIG. 1C). The cross-section in the chin area 2a, in particular in the area of the middle 7, is reduced in width (between the longer sides) so that, when the ear protector 1 is pulled apart for application, the deformation will mainly occur in the chin area. The transitions between the various arrangements according to FIG. 1A to 1C merge seamlessly and without any sharp edges where potential fractures may occur.

The horseshoe shape of the band 2 is, when seen from above (FIG. 3), supported by a horizontal angle χ (top view in FIG. 3) at which the centre lines 2a' and 2b' of the chin and cheek areas 2a, 2b meet. This angle χ ranges from 135° to 170°, preferably from 140 to 170°, and even more preferably from 150° to 170°, and preferably 165±1 to 2°.

The axis of rotation 3' through the support 3 extends at an angle δ which, when seen in a front view, is inclined upwards and which amounts to approx. 70°. At the point where the support 3 is fastened to the connection area 2c, said connection area 2c is enlarged, in the vertical direction, so as to form a location of attachment 9 so that the axis of rotation 3' extends through the enlarged area.

FIG. 5 shows the position of the ear protector according to the present invention on the user. The broken line indicates the position and the approximate outer contour of a lower jaw bone 8 comprising the corpus mandibulae 8a and the ramus mandibulae 8b. It can clearly be seen that the ear protector 1 according to the present invention is adapted to the shape, i.e. the outer contour of the lower jaw bone 8; the chin area 2a can be oriented substantially parallel to the lower boundary of the corpus mandibulae 6a, and the cheek area 2b follows the rise of the ramus mandibulae 8b at this position.

The connection area 2c bridges the distance between the approximate position of the temporomandibular joint and the user's outer ear canal. As can clearly be seen from FIG. 5, the ear protector 1 according to the present invention offers a good freedom of neck movement, i.e. the chin area 2a extends at the preferred position, which is indicated by solid lines, a good deal above a possibly existing collar so that a noise-transmitting rubbing on the clothes will be less likely, even if the user should incline his head very strongly. The structural design according to the present invention also has the effect that the centre of gravity is displaced in a direction closer to the axis of rotation 3 so that, even under the influence of the normally occurring vibrations, there will be less risk that the ear protector will automatically swivel downwards.

As a modification of the embodiment described and shown hereinbefore, the fastening of the earplugs with the aid of the thread on the support can also be used for ear protectors having a conventional band. In addition, the connection area can be dispensed with, if desired, and the cheek area can lead directly from the chin area to the support. The specially indicated, preferred dimensions can also be varied within the range specified for various head sizes. The cross-sectional configurations can be adapted as well.

The invention claimed is:

1. An ear protector (1) comprising a resilient band (2), the free ends of which each have arranged thereon an earplug (4), said band (2) including a first area (2a) whose centre line (2a') merges under an angle (a) with an additional area (2b), and said band (2) being pivotable, when in use, in the user's ears about an axis of rotation (3') extending through the earplugs (4), characterized in that the first area is configured as a chin area (2a) and the additional area as a cheek area (2b), that the angle (a) ranges from 45° to 70° and that the length (L) of the cheek area (2b) is dimensioned such that an extension of the centre line (2a') of the chin area (2a) and a line (5'), which is parallel to said centre line (2a') and which extends through the point of penetration (D) of the axis of rotation (3') through the band (2), are spaced apart at a distance (A) which ranges from 40 to 60 mm.

2. An ear protector (1) according to claim 1, characterized in that the band (2) includes a connection area (2c) between the cheek area (2b) and the earplugs (4), the centre line (2c') of said connection area (2c) extending substantially parallel to the centre line (2a') of the chin area (2a) with a deviation of less than 5°.

3. An ear protector (1) according to claim 1, characterized in that the point of penetration (D) of the axis of rotation (3') through the band (2) is spaced apart from a line (6'), which extends at right angles to the centre line (2a') of the chin area (2a) through the point of intersection (S1) of said centre line (2a') with the centre line (2b') of the cheek area (2b), at a distance (B) which ranges from 60 to 80 mm.

4. An ear protector (1) according to claim 1, characterized in that the cheek area (2b) extends substantially straight.

5. An ear protector (1) according to claim 1, characterized in that the cheek area (2b) has a length (L) of 45 mm to 55 mm.

6. An ear protector (1) according to claim 1, characterized in that the chin area (2a) extends essentially in one plane.

7. An ear protector (1) according to claim 1, characterized in that the chin area (2a) merges with the cheek area (2b) via a curved portion.

8. An ear protector (1) according to claim 1, characterized in that the length (E) of the chin area (2a) is between 60 mm and 100 mm between the front end (7) and a connection line extending between the points of intersection (S1) of the centre lines (2a', 2b') of the chin and cheek areas (2a, 2b).

9. An ear protector (1) according to claim 1, characterized in that the cheek area (2b) merges via a curved portion with a connection area (2c) to the earplugs (4).

10. An ear protector (1) according to claim 1, characterized in that the chin area (2a) is bent into a parabola shape.

11. An ear protector (1) according to claim 1, characterized in that the centre line (2b') of the cheek area (2b) merges with the centre line (2a') of the chin area (2a) under a horizontal angle (X) of 130° to 185°.

12. An ear protector (1) according to claim 1, characterized in that the earplugs (4) are releasably fixed to a support (3).

13. An ear protector (1) according to claim 1, characterized in that the earplugs (4) are releasably fixed to a threaded support (3).

* * * * *